(12) United States Patent
Ashby et al.

(10) Patent No.: US 10,932,517 B2
(45) Date of Patent: Mar. 2, 2021

(54) PRESSURE SENSOR TO QUANTIFY WORK

(71) Applicant: ICON Health & Fitness, Inc., Logan, UT (US)

(72) Inventors: Darren C. Ashby, Richmond, UT (US); Scott R. Watterson, Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 6 days.

(21) Appl. No.: 16/508,860

(22) Filed: Jul. 11, 2019

(65) Prior Publication Data

US 2019/0328079 A1 Oct. 31, 2019

Related U.S. Application Data

(63) Continuation of application No. 14/641,663, filed on Mar. 9, 2015, now Pat. No. 10,433,612.

(Continued)

(51) Int. Cl.
*A43B 5/14* (2006.01)
*A43B 3/00* (2006.01)
(Continued)

(52) U.S. Cl.
CPC ............. *A43B 5/14* (2013.01); *A43B 3/0005* (2013.01); *A43B 3/0015* (2013.01); *A61B 5/6807* (2013.01); *F03G 5/06* (2013.01); *G01L 1/142* (2013.01); *A63B 21/008* (2013.01); *A63B 21/0085* (2013.01); *A63B 21/012* (2013.01); *A63B 21/22* (2013.01); *A63B 22/0046* (2013.01); *A63B 22/0056* (2013.01); *A63B 22/0605* (2013.01); *A63B 2220/20* (2013.01); *A63B 2220/30* (2013.01); *A63B 2220/40* (2013.01); *A63B 2220/51* (2013.01); *A63B 2220/56* (2013.01); *A63B 2225/50* (2013.01); *A63B 2230/06* (2013.01);
(Continued)

(58) Field of Classification Search
CPC ....... A43B 5/14; A43B 3/0005; A43B 3/0015; G01L 1/142
USPC .......................................................... 702/41
See application file for complete search history.

(56) References Cited

U.S. PATENT DOCUMENTS

| 4,913,396 A | 4/1990 | Dalebout et al. |
| 4,998,725 A | 3/1991 | Watterson et al. |

(Continued)

FOREIGN PATENT DOCUMENTS

| TW | M424795 | 3/2012 |
| TW | M447216 | 2/2013 |
| WO | 2009082215 | 7/2009 |

OTHER PUBLICATIONS

U.S. Appl. No. 13/088,007, filed Apr. 15, 2011, Scott R. Watterson.
(Continued)

*Primary Examiner* — Igwe U Anya
(74) *Attorney, Agent, or Firm* — Ray Quinney & Nebeker

(57) ABSTRACT

A monitoring system includes a shoe and a sole integrated into the shoe. The monitoring system also includes a connection mechanism attached to an underside of the sole and is shaped to connect the sole to a pedal. A pressure sensor is incorporated into the shoe that senses a force exerted on the pedal when the shoe is connected to the pedal through the connection mechanism.

20 Claims, 6 Drawing Sheets

Related U.S. Application Data

(60) Provisional application No. 61/950,606, filed on Mar. 10, 2014.

(51) Int. Cl.
  A61B 5/00 (2006.01)
  F03G 5/06 (2006.01)
  G01L 1/14 (2006.01)
  A63B 21/008 (2006.01)
  A63B 21/012 (2006.01)
  A63B 22/00 (2006.01)
  A63B 22/06 (2006.01)
  B62M 3/08 (2006.01)
  B62M 6/50 (2010.01)
  B62J 45/40 (2020.01)
  A63B 21/22 (2006.01)

(52) U.S. Cl.
  CPC ..... *A63B 2230/207* (2013.01); *A63B 2230/30* (2013.01); *A63B 2230/75* (2013.01); *B62J 45/40* (2020.02); *B62M 3/08* (2013.01); *B62M 6/50* (2013.01)

(56) References Cited

U.S. PATENT DOCUMENTS

| | | |
|---|---|---|
| 5,046,382 A | 9/1991 | Steinberg |
| 5,062,627 A | 11/1991 | Bingham |
| 5,062,633 A | 11/1991 | Engel et al. |
| 5,067,710 A | 11/1991 | Watterson et al. |
| 5,149,312 A | 9/1992 | Croft et al. |
| 5,192,255 A | 3/1993 | Dalebout et al. |
| 5,247,853 A | 9/1993 | Dalebout |
| 5,279,528 A | 1/1994 | Dalebout et al. |
| 5,372,559 A | 12/1994 | Dalebout et al. |
| 5,409,435 A | 4/1995 | Daniels |
| 5,489,249 A | 2/1996 | Brewer et al. |
| 5,512,025 A | 4/1996 | Dalebout et al. |
| 5,527,245 A | 6/1996 | Dalebout |
| 5,529,553 A | 6/1996 | Finlayson |
| 5,595,556 A | 1/1997 | Dalebout et al. |
| 5,607,375 A | 3/1997 | Dalebout |
| 5,622,527 A | 4/1997 | Watterson et al. |
| 5,645,509 A | 7/1997 | Brewer et al. |
| 5,662,557 A | 9/1997 | Watterson et al. |
| 5,669,857 A | 9/1997 | Watterson et al. |
| 5,672,140 A | 9/1997 | Watterson et al. |
| 5,674,156 A | 10/1997 | Watterson et al. |
| 5,674,453 A | 10/1997 | Watterson et al. |
| 5,676,624 A | 10/1997 | Watterson et al. |
| 5,683,332 A | 11/1997 | Watterson et al. |
| 5,702,325 A | 12/1997 | Watterson et al. |
| 5,704,879 A | 1/1998 | Watterson et al. |
| 5,718,657 A | 2/1998 | Dalebout et al. |
| 5,720,200 A | 2/1998 | Anderson et al. |
| 5,743,833 A | 4/1998 | Watterson et al. |
| 5,762,584 A | 6/1998 | Daniels |
| 5,762,587 A | 6/1998 | Dalebout et al. |
| 5,772,560 A | 6/1998 | Watterson et al. |
| 5,813,142 A | 9/1998 | Demon |
| 5,827,155 A | 10/1998 | Jensen |
| 5,860,893 A | 1/1999 | Watterson et al. |
| 5,860,894 A | 1/1999 | Dalebout et al. |
| 5,899,834 A | 5/1999 | Dalebout et al. |
| 5,951,441 A | 9/1999 | Dalebout |
| 6,019,710 A | 2/2000 | Dalebout et al. |
| 6,033,347 A | 3/2000 | Dalebout et al. |
| 6,059,692 A | 5/2000 | Hickman |
| 6,174,267 B1 | 1/2001 | Dalebout |
| 6,193,631 B1 | 2/2001 | Hickman |
| 6,280,362 B1 | 8/2001 | Dalebout et al. |
| 6,312,363 B1 | 11/2001 | Watterson et al. |
| 6,350,218 B1 | 2/2002 | Dalebout et al. |
| 6,447,424 B1 | 9/2002 | Ashby et al. |
| 6,458,060 B1 | 10/2002 | Watterson et al. |
| 6,471,622 B1 | 10/2002 | Hammer et al. |
| 6,601,016 B1 | 7/2003 | Brown et al. |
| 6,626,799 B2 | 9/2003 | Watterson et al. |
| 6,652,424 B2 | 11/2003 | Dalebout |
| 6,701,271 B2 | 3/2004 | Willner et al. |
| 6,702,719 B1 | 3/2004 | Brown et al. |
| 6,730,002 B2 | 5/2004 | Hald et al. |
| 6,743,153 B2 | 6/2004 | Watterson et al. |
| 6,746,371 B1 | 6/2004 | Brown et al. |
| 6,749,537 B1 | 6/2004 | Hickman |
| 6,761,667 B1 | 7/2004 | Cutler et al. |
| 6,786,852 B2 | 9/2004 | Watterson et al. |
| 6,808,472 B1 | 10/2004 | Hickman |
| 6,821,230 B2 | 11/2004 | Dalebout et al. |
| 6,830,540 B2 | 12/2004 | Watterson |
| 6,863,641 B1 | 3/2005 | Brown et al. |
| 6,866,613 B1 | 3/2005 | Brown et al. |
| 6,875,160 B2 | 4/2005 | Watterson et al. |
| 6,918,858 B2 | 7/2005 | Watterson et al. |
| 6,921,351 B1 | 7/2005 | Hickman et al. |
| 6,974,404 B1 | 12/2005 | Watterson et al. |
| 6,997,852 B2 | 2/2006 | Watterson et al. |
| 7,052,442 B2 | 5/2006 | Watterson |
| 7,060,006 B1 | 6/2006 | Watterson et al. |
| 7,060,008 B2 | 6/2006 | Watterson et al. |
| 7,070,539 B2 | 7/2006 | Brown et al. |
| 7,097,588 B2 | 8/2006 | Watterson |
| 7,128,693 B2 | 10/2006 | Brown et al. |
| 7,166,062 B1 | 1/2007 | Watterson et al. |
| 7,166,064 B2 | 1/2007 | Watterson et al. |
| 7,169,087 B2 | 1/2007 | Ercanbrack et al. |
| 7,192,388 B2 | 3/2007 | Dalebout et al. |
| 7,285,075 B2 | 10/2007 | Cutler et al. |
| 7,344,481 B2 | 3/2008 | Watterson et al. |
| 7,377,882 B2 | 5/2008 | Watterson |
| 7,425,188 B2 | 9/2008 | Ercanbrack |
| 7,455,622 B2 | 11/2008 | Watterson et al. |
| 7,510,509 B2 | 3/2009 | Hickman |
| 7,537,546 B2 | 5/2009 | Watterson et al. |
| 7,537,549 B2 | 5/2009 | Nelson et al. |
| 7,540,828 B2 | 6/2009 | Watterson et al. |
| 7,549,947 B2 | 6/2009 | Hickman et al. |
| 7,556,590 B2 | 7/2009 | Watterson et al. |
| 7,563,203 B2 | 7/2009 | Dalebout et al. |
| 7,575,536 B1 | 8/2009 | Hickman |
| 7,604,573 B2 | 10/2009 | Dalebout et al. |
| 7,618,350 B2 | 11/2009 | Dalebout et al. |
| 7,625,315 B2 | 12/2009 | Hickman |
| 7,628,730 B1 | 12/2009 | Watterson et al. |
| 7,637,847 B1 | 12/2009 | Hickman |
| 7,645,212 B2 | 1/2010 | Ashby et al. |
| 7,645,213 B2 | 1/2010 | Watterson |
| 7,674,205 B2 | 3/2010 | Dalebout et al. |
| 7,713,171 B1 | 5/2010 | Hickman |
| 7,713,172 B2 | 5/2010 | Watterson et al. |
| 7,736,279 B2 | 6/2010 | Dalebout et al. |
| 7,740,563 B2 | 6/2010 | Dalebout et al. |
| 7,766,797 B2 | 8/2010 | Dalebout |
| 7,775,940 B2 | 8/2010 | Dalebout et al. |
| 7,789,800 B1 | 9/2010 | Watterson et al. |
| 7,815,550 B2 | 10/2010 | Watterson et al. |
| 7,837,595 B2 | 11/2010 | Rice |
| 7,839,058 B1 | 11/2010 | Churchill |
| 7,857,731 B2 | 12/2010 | Hickman et al. |
| 7,862,475 B2 | 1/2011 | Watterson |
| 7,862,478 B2 | 1/2011 | Watterson et al. |
| 7,862,483 B2 | 1/2011 | Hendrickson et al. |
| 7,901,330 B2 | 3/2011 | Dalebout et al. |
| 7,909,740 B2 | 3/2011 | Dalebout et al. |
| 7,980,996 B2 | 7/2011 | Hickman |
| 7,981,000 B2 | 7/2011 | Watterson et al. |
| 7,985,164 B2 | 7/2011 | Ashby |
| 8,011,242 B2 | 9/2011 | O'neill |
| 8,029,415 B2 | 10/2011 | Ashby et al. |
| 8,033,959 B2 | 10/2011 | Oleson et al. |
| 8,122,773 B2 | 2/2012 | Wyatt |
| 8,251,874 B2 | 8/2012 | Ashby et al. |
| 8,298,123 B2 | 10/2012 | Hickman |

(56) References Cited

U.S. PATENT DOCUMENTS

| | | |
|---|---|---|
| 8,327,723 B2 | 12/2012 | Roudergues |
| 8,370,087 B2 | 2/2013 | Zhu |
| 8,387,470 B2 | 3/2013 | Tuulari |
| 8,584,520 B2 | 11/2013 | Kokkoneva |
| 8,690,735 B2 | 4/2014 | Watterson et al. |
| 8,758,201 B2 | 6/2014 | Ashby et al. |
| 8,762,077 B2 | 6/2014 | Redmond |
| 8,784,270 B2 | 7/2014 | Watterson |
| 8,808,148 B2 | 8/2014 | Watterson |
| 8,845,493 B2 | 9/2014 | Watterson et al. |
| 8,876,668 B2 | 11/2014 | Hendrickson et al. |
| 8,894,549 B2 | 11/2014 | Colledge |
| 8,911,330 B2 | 12/2014 | Watterson et al. |
| 8,920,288 B2 | 12/2014 | Dalebout |
| 8,986,165 B2 | 3/2015 | Ashby |
| 8,992,364 B2 | 3/2015 | Law et al. |
| 8,992,387 B2 | 3/2015 | Watterson et al. |
| 9,028,368 B2 | 5/2015 | Ashby et al. |
| 9,028,370 B2 | 5/2015 | Watterson |
| 9,039,578 B2 | 5/2015 | Dalebout |
| 9,063,026 B2 | 6/2015 | Nassef |
| 9,072,930 B2 | 7/2015 | Ashby et al. |
| 9,119,983 B2 | 9/2015 | Rhea |
| 9,123,317 B2 | 9/2015 | Watterson et al. |
| 9,138,615 B2 | 9/2015 | Olson et al. |
| 9,142,139 B2 | 9/2015 | Watterson et al. |
| 9,149,683 B2 | 9/2015 | Smith |
| 9,186,549 B2 | 11/2015 | Watterson et al. |
| 9,254,416 B2 | 2/2016 | Ashby |
| 9,278,248 B2 | 3/2016 | Tyger |
| 9,278,250 B2 | 3/2016 | Buchanan |
| 9,289,648 B2 | 3/2016 | Watterson |
| 9,331,559 B2 | 5/2016 | Shastry |
| 9,339,691 B2 | 5/2016 | Brammer |
| 9,352,185 B2 | 5/2016 | Hendrickson et al. |
| 9,352,186 B2 | 5/2016 | Watterson |
| 9,375,605 B2 | 6/2016 | Tyger |
| 9,381,394 B2 | 7/2016 | Mortensen et al. |
| 9,387,387 B2 | 7/2016 | Dalebout |
| 9,403,051 B2 | 8/2016 | Cutler |
| 9,421,416 B2 | 8/2016 | Mortensen et al. |
| 9,457,222 B2 | 10/2016 | Dalebout |
| 9,460,632 B2 | 10/2016 | Watterson |
| 9,463,356 B2 | 10/2016 | Rhea |
| 9,468,798 B2 | 10/2016 | Dalebout |
| 9,480,874 B2 | 11/2016 | Cutler |
| 9,492,704 B2 | 11/2016 | Mortensen et al. |
| 9,517,378 B2 | 12/2016 | Ashby et al. |
| 9,521,901 B2 | 12/2016 | Dalebout |
| 9,579,544 B2 | 2/2017 | Watterson |
| 9,586,086 B2 | 3/2017 | Dalebout et al. |
| 9,586,090 B2 | 3/2017 | Watterson et al. |
| 9,604,099 B2 | 3/2017 | Taylor |
| 9,616,278 B2 | 4/2017 | Olson |
| 9,623,281 B2 | 4/2017 | Hendrickson |
| 9,636,567 B2 | 5/2017 | Brammer et al. |
| 9,675,839 B2 | 6/2017 | Dalebout |
| 9,682,307 B2 | 6/2017 | Dalebout |
| 9,694,234 B2 | 7/2017 | Dalebout et al. |
| 9,694,242 B2 | 7/2017 | Ashby |
| 9,737,755 B2 | 8/2017 | Dalebout |
| 9,767,785 B2 | 9/2017 | Ashby |
| 9,808,672 B2 | 11/2017 | Dalebout |
| 9,878,210 B2 | 1/2018 | Watterson |
| 9,889,334 B2 | 2/2018 | Ashby et al. |
| 9,937,376 B2 | 4/2018 | McInelly et al. |
| 9,937,377 B2 | 4/2018 | McInelly et al. |
| 9,937,378 B2 | 4/2018 | Dalebout et al. |
| 9,937,379 B2 | 4/2018 | Mortensen |
| 9,943,722 B2 | 4/2018 | Dalebout |
| 9,968,821 B2 | 5/2018 | Finlayson et al. |
| 9,968,823 B2 | 5/2018 | Cutler |
| 10,010,755 B2 | 7/2018 | Watterson |
| 10,010,756 B2 | 7/2018 | Watterson |
| 10,046,196 B2 | 8/2018 | Ercanbrack |
| 10,071,285 B2 | 9/2018 | Smith et al. |
| 10,085,586 B2 | 10/2018 | Smith et al. |
| 10,186,161 B2 | 1/2019 | Watterson |
| 10,207,143 B2 | 2/2019 | Dalebout |
| 10,207,145 B2 | 2/2019 | Tyger |
| 10,207,147 B2 | 2/2019 | Ercanbrack |
| 10,207,148 B2 | 2/2019 | Powell |
| 10,220,259 B2 | 3/2019 | Brammer |
| 10,252,109 B2 | 4/2019 | Watterson |
| 10,272,317 B2 | 4/2019 | Watterson |
| 10,279,212 B2 | 5/2019 | Dalebout et al. |
| 10,293,211 B2 | 5/2019 | Watterson et al. |
| 10,343,017 B2 | 7/2019 | Jackson |
| 10,376,736 B2 | 8/2019 | Powell et al. |
| 2006/0248965 A1 | 11/2006 | Wyatt |
| 2008/0229875 A1 | 9/2008 | Ray |
| 2009/0308179 A1* | 12/2009 | Wyatt ............... A61B 5/0002 |
| | | 73/862.391 |
| 2010/0242246 A1 | 9/2010 | Dalebout et al. |
| 2011/0054359 A1 | 3/2011 | Sazonov et al. |
| 2012/0237911 A1 | 9/2012 | Watterson |
| 2012/0253234 A1* | 10/2012 | Yang ............... A61B 5/1038 |
| | | 600/595 |
| 2013/0154441 A1 | 6/2013 | Redmond |
| 2013/0165195 A1 | 6/2013 | Watterson |
| 2013/0172152 A1 | 7/2013 | Watterson |
| 2013/0172153 A1 | 7/2013 | Watterson |
| 2013/0178334 A1 | 7/2013 | Brammer |
| 2013/0190136 A1 | 7/2013 | Watterson |
| 2013/0196298 A1 | 8/2013 | Watterson |
| 2013/0196821 A1 | 8/2013 | Watterson et al. |
| 2013/0196822 A1 | 8/2013 | Watterson et al. |
| 2013/0218585 A1 | 8/2013 | Watterson |
| 2013/0281241 A1 | 10/2013 | Watterson |
| 2014/0024499 A1 | 1/2014 | Watterson |
| 2014/0135173 A1 | 5/2014 | Watterson |
| 2014/0274574 A1 | 9/2014 | Shorten et al. |
| 2014/0274579 A1 | 9/2014 | Olson |
| 2014/0309085 A1 | 10/2014 | Watterson et al. |
| 2015/0177083 A1* | 6/2015 | Redmond ............ A43B 3/0005 |
| | | 702/44 |
| 2015/0182781 A1 | 7/2015 | Watterson |
| 2015/0238817 A1 | 8/2015 | Watterson |
| 2015/0250418 A1 | 9/2015 | Ashby |
| 2015/0251055 A1 | 9/2015 | Ashby |
| 2015/0253210 A1 | 9/2015 | Ashby et al. |
| 2015/0253735 A1 | 9/2015 | Watterson |
| 2015/0253736 A1 | 9/2015 | Watterson |
| 2015/0258560 A1 | 9/2015 | Ashby |
| 2015/0352396 A1 | 12/2015 | Dalebout |
| 2016/0058335 A1 | 3/2016 | Ashby |
| 2016/0063615 A1 | 3/2016 | Watterson |
| 2016/0092909 A1 | 3/2016 | Watterson |
| 2016/0107065 A1 | 4/2016 | Brammer |
| 2016/0121074 A1 | 5/2016 | Ashby |
| 2016/0148535 A1 | 5/2016 | Ashby |
| 2016/0148536 A1 | 5/2016 | Ashby |
| 2016/0158595 A1 | 6/2016 | Dalebout |
| 2016/0206922 A1 | 7/2016 | Dalebout et al. |
| 2016/0250519 A1 | 9/2016 | Watterson |
| 2016/0253918 A1 | 9/2016 | Watterson |
| 2017/0056715 A1 | 3/2017 | Dalebout et al. |
| 2017/0193578 A1 | 7/2017 | Watterson |
| 2017/0266483 A1 | 9/2017 | Dalebout et al. |
| 2017/0266532 A1 | 9/2017 | Watterson |
| 2017/0266533 A1 | 9/2017 | Dalebout |
| 2017/0270820 A1 | 9/2017 | Ashby |
| 2018/0001135 A1 | 1/2018 | Powell |
| 2018/0036585 A1 | 2/2018 | Powell |
| 2018/0084817 A1 | 3/2018 | Capell et al. |
| 2018/0085630 A1 | 3/2018 | Capell et al. |
| 2018/0089396 A1 | 3/2018 | Capell et al. |
| 2018/0099116 A1 | 4/2018 | Ashby |
| 2018/0099179 A1 | 4/2018 | Chatterton et al. |
| 2018/0099180 A1 | 4/2018 | Wilkinson |
| 2018/0099205 A1 | 4/2018 | Watterson |
| 2018/0111034 A1 | 4/2018 | Watterson |
| 2018/0117385 A1 | 5/2018 | Watterson |
| 2018/0117393 A1 | 5/2018 | Ercanbrack |

(56) References Cited

U.S. PATENT DOCUMENTS

| | | |
|---|---|---|
| 2018/0154205 A1 | 6/2018 | Watterson |
| 2018/0154207 A1 | 6/2018 | Hochstrasser |
| 2018/0154208 A1 | 6/2018 | Powell et al. |
| 2018/0154209 A1 | 6/2018 | Watterson |
| 2019/0058370 A1 | 2/2019 | Tinney |
| 2019/0080624 A1 | 3/2019 | Watterson |
| 2019/0151698 A1 | 5/2019 | Olson |
| 2019/0168072 A1 | 6/2019 | Brammer |
| 2019/0192898 A1 | 6/2019 | Dalebout |
| 2019/0192952 A1 | 6/2019 | Powell |
| 2019/0209893 A1 | 7/2019 | Watterson |
| 2019/0223612 A1 | 7/2019 | Watterson |

OTHER PUBLICATIONS

U.S. Appl. No. 16/351,156, filed Mar. 12, 2019, William T. Dalebout.
U.S. Appl. No. 16/378,022, filed Apr. 8, 2019, William T. Dalebout.
U.S. Appl. No. 16/435,104, filed Jun. 7, 2019, Dale Alan Buchanan.
International Search Report and Written Opinion issued in PCT Application PCT/US2015/019492 dated May 22, 2015.
Taiwan Search Report and Office Action issued in application No. 104107623 dated Mar. 16, 2016.

\* cited by examiner

PRESSURE SENSOR TO QUANTIFY WORK

RELATED APPLICATIONS

This application is a continuation of U.S. patent application Ser. No. 14/641,663 titled "Pressure Sensor to Quantify Work" filed on Mar. 9, 2015, which claims priority to U.S. provisional Patent Application No. 61/950,606 titled "Pressure Sensor to Quantify Work" filed Mar. 10, 2014 and these applications are herein incorporated by reference for all that they disclose.

BACKGROUND

To propel a bicycle, a user sits on a seat and straddles a frame with his or her legs. A pair of pedals are connected to each other with a pair of crank arms that are connected to a gear assembly. The pedals are positioned to be engaged by the feet and to travel in a reciprocating motion powered by the user's feet. The gear assembly directs the energy exerted through the user's feet to an axle of one of the wheels of the bicycle, which causes the wheel to turn. Such rotation of the wheel propels the bicycle forward. The speed at which the bicycle travels is dependent on the amount of resistance on the bicycle and the amount of energy that the user exerts with his or her legs to rotate the wheel. The resistance on the bicycle generally includes the collective weight of the bicycle and the user as well as the slope of the terrain on which the bicycle is being propelled. In the case of a stationary bicycle, the resistance may be provided with a magnetic resistance mechanism, a pneumatic resistance mechanism, a hydraulic resistance mechanism, a gear type resistance mechanism, braking pads, tensioning elements, fan blades, another type of resistance mechanism, or combinations thereof.

One mechanism for measuring the amount of energy exerted by the user is disclosed in U.S. Patent Publication No. 2003/0074985 issued to Gordon Liao. In this reference, a sensor of the pedaling force of a power-assisting bike includes a transmission system provided with at least one pair of screw gears. One of the screw gears is activated by the pedaling force to rotate at an original location and the other driven by a screw gear engaging to rotate and shift along a shaft, with a resilience member fitted at an end side. An annular magnet is fitted around the end of the shaft of the resilience member and the screw gear, capable to shift together with the screw gear. A Hall sensor is provided on a fixed side of the annular magnet. Thus, the lateral force produced by the screw gears can detect an axially shifting distance of the screw gear and give out a voltage signal to control a motor to output motive power for the bike. Another type of mechanism for measuring the amount of energy exerted by the user is described in U.S. Pat. No. 8,011,242 issued to George David O'Neill. Each of these references are herein incorporated by reference for all that they disclose.

SUMMARY

In a preferred embodiment of the invention, a monitoring system includes a shoe and a sole integrated into the shoe. The monitoring system also includes a connection mechanism attached to an underside of the sole and is shaped to connect the sole to a pedal. A pressure sensor is incorporated into the shoe that senses a force exerted on the pedal when the shoe is connected to the pedal through the connection mechanism.

In one aspect of the invention, the pressure sensor distinguishes between upward forces and downward forces.

In one aspect of the invention, the shoe also comprises an accelerometer that senses a direction of the force exerted on the pedal.

In one aspect of the invention, the shoe also comprises a wireless transmitter that transmits measurements of the pressure sensor to a computing device.

In one aspect of the invention, the computing device comprises a processor and memory with programmed instructions where the programmed instructions cause the processor to quantify the force based at least in part on the measurements of the pressure sensor.

In one aspect of the invention, the programmed instructions further cause the processor to quantify a calorie count based at least in part on the measurements of the pressure sensor.

In one aspect of the invention, the connection mechanism is a clipless pedal system.

In one aspect of the invention, the pressure sensor is positioned proximate a cleat receptacle of the clipless pedal system.

In one aspect of the invention, the pressure sensor is a capacitive based pressure sensor.

In one aspect of the invention, the capacitive based pressure sensor comprises electrically conducting plates that are spaced a distance from each other, wherein the electrically conducting plates move such that the distance narrows during a downward force and the distance widens during an upward force.

In one aspect of the invention, the shoe further comprises an energy harvesting mechanism that converts a motion of the shoe into electrical power when the shoe is in motion.

In one aspect of the invention, the shoe further comprises an energy harvesting mechanism that converts a pressure exerted onto the sole into electrical power.

In one aspect of the invention, a monitoring system may include a shoe.

In one aspect of the invention, a sole integrated into the shoe.

In one aspect of the invention, a clipless pedal system that connects the sole to a pedal when the pedal is attached to the clipless pedal system.

In one aspect of the invention, a pressure sensor incorporated into the shoe and positioned proximate a cleat receptacle of the clipless pedal system.

In one aspect of the invention, the pressure sensor senses a force exerted on the pedal.

In one aspect of the invention, the pressure sensor distinguishes between upward forces and downward forces.

In one aspect of the invention, the shoe further comprises an energy harvesting mechanism that supplies the pressure sensor with electrical power.

In one aspect of the invention, the shoe also comprises an accelerometer that that senses a direction of the force exerted on the pedal.

In one aspect of the invention, the shoe also comprises a wireless transmitter that transmits measurements of the pressure sensor to a computing device.

In one aspect of the invention, the computing device comprises a processor and memory with programmed instructions that cause the processor to quantify the force based at least in part on the measurements of the pressure sensor.

In one aspect of the invention, the programmed instructions further cause the processor to quantify a calorie count based at least in part on the measurements of the pressure sensor.

In one aspect of the invention, the pressure sensor is a capacitive based pressure sensor.

In one aspect of the invention, the capacitive based pressure sensor comprises electrically conducting plates that are spaced a distance from each other, wherein the electrically conducting plates move such that the distance narrows during a downward force to the pedal and the distance widens during an upward force to the pedal.

In one aspect of the invention, a monitoring system may comprise a shoe.

In one aspect of the invention, a sole integrated into the shoe.

In one aspect of the invention, a clipless pedal system that connects the sole to a pedal when the pedal is attached to the clipless pedal system.

In one aspect of the invention, a capacitive based pressure sensor incorporated into the shoe and positioned proximate a cleat receptacle of the clipless pedal system.

In one aspect of the invention, the capacitive based pressure sensor that senses a force exerted on the pedal wherein the capacitive based pressure sensor distinguishes between upward forces to the pedal through the shoe and downward forces to the pedal through the shoe.

In one aspect of the invention, the shoe further comprises an energy harvesting mechanism that supplies the capacitive based pressure sensor with electrical power.

In one aspect of the invention, an accelerometer incorporated into the shoe that senses a direction of the force exerted on the pedal.

In one aspect of the invention, the capacitive based pressure sensor comprises electrically conducting plates that are spaced a distance from each other, wherein the electrically conducting plates move such that the distance narrows during a downward force on the pedal and the distance widens during an upward force to the pedal.

In one aspect of the invention, a wireless transmitter incorporated into the shoe that transmits measurements of the capacitive based pressure sensor to a computing device.

In one aspect of the invention, the computing device comprises a processor and memory with programmed instructions.

In one aspect of the invention, the programmed instructions cause the processor to quantify the force based at least in part on the measurements of the capacitive based pressure sensor.

In one aspect of the invention, the programmed instructions cause the processor to quantify a calorie count based at least in part on the measurements of the capacitive based pressure sensor.

Any of the aspects of the invention detailed above may be combined with any other aspect of the invention detailed herein.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
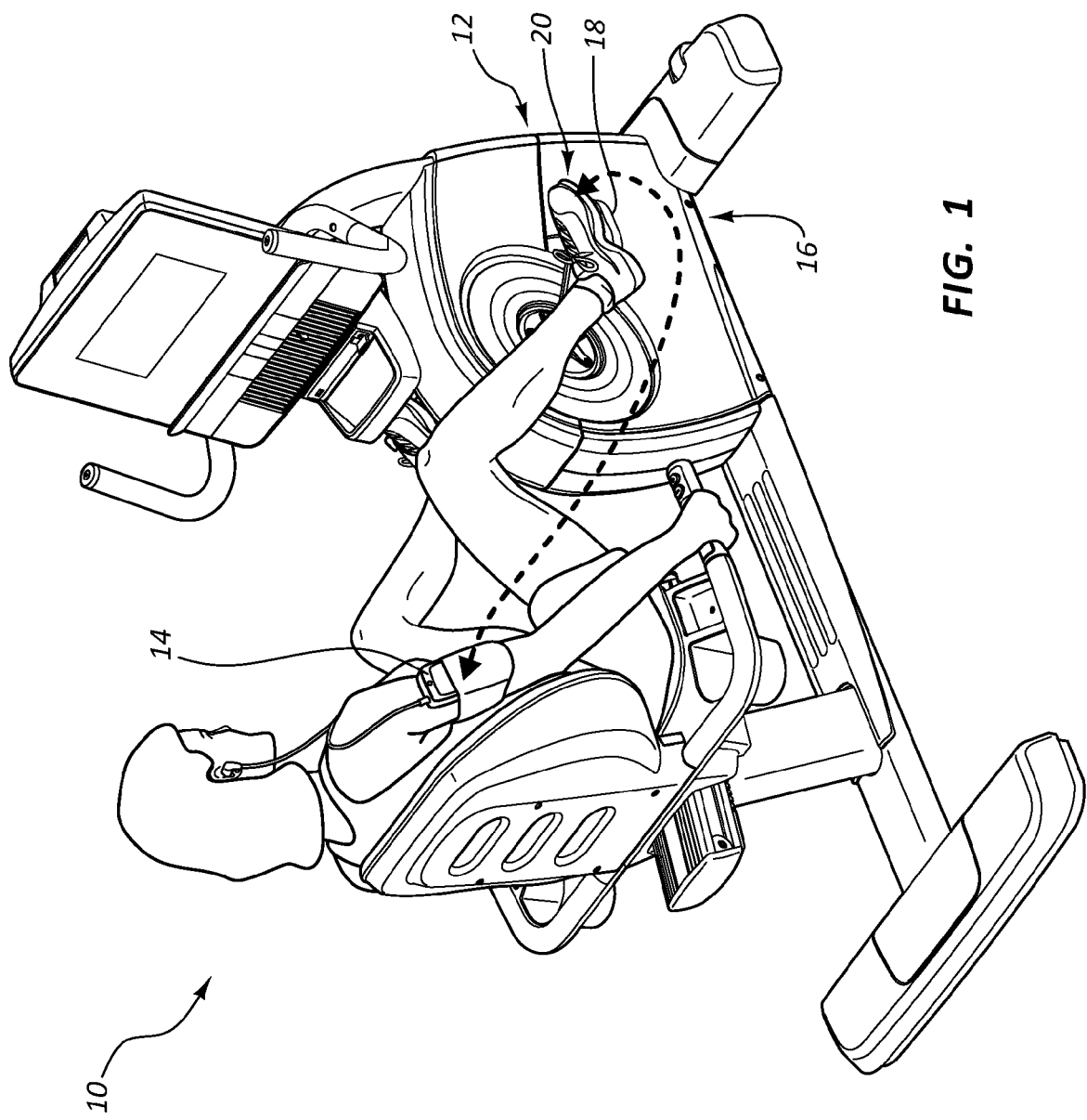
FIG. 1 illustrates a perspective view of an example of a stationary bike in accordance with the present disclosure.

Clipless bicycle pedals allow a rigid attachment to be made between a user's shoe and the pedal. Often, clipless bicycle pedals are used in lieu of straps that hold the user's shoe to the pedal as the user pulls up, thus keeping the shoe and the pedal together. These straps that are attached to the pedals stretch as the shoe is raised. As a result, some of the energy exerted by the user to pull up on the pedal through the strap is lost. Further, there is often a gap between the underside of the strap and the top of the user's shoe. Thus, to pull up on the strap with the shoe, the shoe may have be lifted off of the pedal to make contact with the strap's underside. The effort exerted to lift the shoe to the underside of the strap also does not contribute to the movement of the pedals. As a result, more energy is lost in the system. The clipless pedals are constructed to minimize such inefficiencies.

Often, the clipless pedals attach to a specialized shoe that can be locked to the pedal. In some cases, the shoe includes a cleat receptacle that can receive a cleat secured to the pedal. The cleats are often attached to the pedal with one or more bolts. Some shoes with cleat receptacles lock onto the cleat when the user steps firmly onto the pedal in a vertical direction, and the shoe unlocks when the user twists his or her heel outward. Often, the shoes associated with the clipless pedals have rigid soles to maximize efficiency and transfer power to the pedals.

The principles described in the present disclosure include a monitoring system that can measure the amount of work performed by a user on a bicycle. Such a system may be used for bicycles that can be propelled by the user's work, such as a road bicycle or a mountain bicycle. Also, the monitoring system may be incorporated into a stationary bicycle. The monitoring system includes a shoe with a sole that has an underside shaped to attach to a connection mechanism, such as a cleat of a pedal associated with a clipless pedal system. A pressure sensor is also incorporated into the shoe and senses a force exerted on the pedal. In some instances, the pressure sensor senses both upward forces and downward forces exerted by the user. An accelerometer can be used to determine the direction of the force. But, in some examples, the arrangement of the pressure sensor can distinguish between upward forces and downward forces without the assistance of an accelerometer.

The shoe can be in wireless communication with a mobile device or a control module of the stationary bicycle. The values measured with the pressure sensor can be sent to such remote devices where calculations about the amount of work performed by the user are calculated. Such calculations may be used to determine a number of calories burned by the user.

The energy to power the pressure sensor, accelerometer, transmitter, and other components of the monitoring system that are in the shoe can be harvested from the work performed by the user. For example, the power can be harvested through a piezoelectric system, a kinetic capture system, another type of system, or combinations thereof. In some examples, the energy levels performed by the components of the monitoring system are kept low so that enough power can be provided through energy harvesting.

For the purposes of this disclosure, terms such as "upward" are used with reference to motions where the pedal is moving in a direction towards the user's knee. Likewise, for the purposes of this disclosure, terms such as "downward" are used with reference to motions where the pedal is moving in a direction away from the user's knee.

Further, for the purposes of this disclosure, the term "connection mechanism" includes a structure on the underside of the shoe that assists in connecting the shoe to the pedal. Such connection mechanisms can include fittings for bicycle cleats, other attachment fittings, cleats, other mechanism, or combinations thereof.

Particularly, with reference to the figures, FIG. 1 illustrates a perspective view of an example of a stationary bicycle 10 in accordance with the present disclosure. In this example, the user is wearing a shoe 12 that includes a pressure sensor that is in wireless communication with a remote device 14. The pressure sensor collects information about the work performed by the user during the workout. The remote device 14 can use the information sent from the shoe 12 to determine results about the user's workout, like calories burned, distance traveled, speed, and other types of information. The calculated results can be presented to the user in real time, such as in a display of the stationary bicycle 10. In some examples, the information and/or the calculated results are updated to a database where the user can retrieve them at a later time.

The measurements collected by the shoe 12 can be sent to the remote device 14 in raw form where the data can be processed. In some examples, some data processing occurs prior to the information being sent to the remote device 14. Such data processing may lower the transmission time or lower the transmission power when transmitting data from the shoe 12 to the remote device 14.

In some embodiments, the shoe 12 takes just pressure measurements. However, in some cases the shoe 12 may also include an accelerometer, another type of sensor, or combinations thereof. The measurements from the accelerometer or other sensors may be sent to the remote device 14 with the measurements from the pressure sensor. Information collected by the accelerometer may be used to improve the pressure sensor calculations. The accelerometer can detect movement of the shoe 12, the direction of the movement, the speed of the movement, and other types of information about the movement that may allow the shoe 12, the remote device 14, or other device to correct for motion artifacts exhibited in the pressure measurements.

The remote device 14 may be part of a mobile device that can perform calculations to determine the amount of work exerted by the user. However, in other examples, the remote device 14 is incorporated into a stationary bicycle 10. Any appropriate type of stationary bicycle 10 may be used in accordance with the principles described in the present disclosure. For example, the stationary bicycle 10 may include a magnetic resistance mechanism, a pneumatic resistance mechanism, a hydraulic resistance mechanism, a gear type resistance mechanism, a pair of braking pads, a tensioning element, a fan blade, another type of resistance mechanism, or combinations thereof. While the examples above have been described with reference to bicycles, the principles described herein may be incorporated into other types of exercise or recreational equipment. For example, the principles described herein may be incorporated into elliptical exercise machines, paddle boats, unicycles, tricycles, stepper machines, other types of foot operated devices, or combinations thereof.

Figure 2:
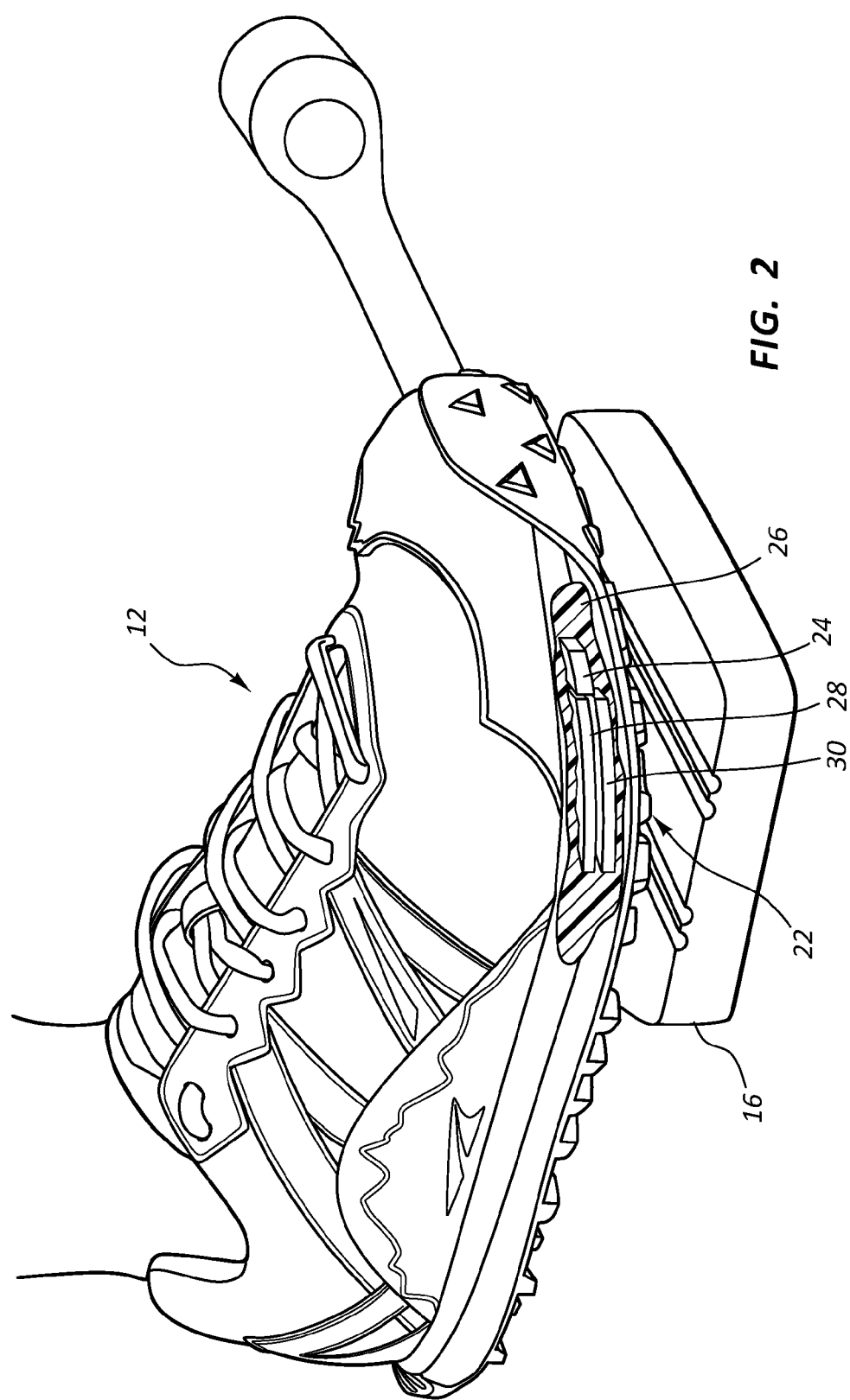
FIG. 2 illustrates a perspective view of an example of a shoe in accordance with the present disclosure.

FIG. 2 illustrates a perspective view of a shoe 12 in accordance with the present disclosure. In this example, the shoe 12 is connected to a pedal 16 through a connection mechanism 18 that is incorporated into a clipless pedal system 20. A pressure sensor 22 and an accelerometer 24 are also incorporated into the shoe 12 and record information while the shoe 12 is secured to the pedal 16 through the clipless pedal system 20.

Any appropriate type of shoe 12 may be used in accordance with the principles described herein. In some examples, the shoe 12 is a cycling shoe 12 that has a sole 26 made of a stiff material to minimize flexing of the sole 26 as a force is transferred from the shoe 12 to the pedal 16. The clipless pedal system 20 includes a cleat receptacle in the sole 26 of the shoe 12. The cleat 27 protrudes upward from the pedal and is shaped to interlock with cleat receptacle of the shoe 12 In some examples, the cleat snaps into a spring loaded mechanism incorporated into the sole 26 of the shoe 12. The cleat may be made of any appropriate material, such as metal, plastic, or other types of material. Further, the cleat may have any appropriate type of shape to interlock with the shoe's sole 26.

Any appropriate type of pedal 16 may be used with the shoe 12 in accordance with the principles described in the present disclosure as long as the pedal 16 is capable of interlocking with the shoe 12 through the connection mechanism 18. In some examples, the pedal 16 can interlock with the shoe 12 on both faces of the pedal, while in other examples, the pedal 16 can interlock with just a single face of the shoe 12.

In the example of FIG. 2, the pressure sensor 22 is positioned above the cleat and comprises a first plate 28 and a second plate 30, which are enlarged for illustrative purposes in the figure. The first and second plates 28, 30 are part of an electrically conductive circuit. The capacitance of the circuit is, in part, dependent on the distance between the first and the second plates 28, 30. The distance between the plates 28, 30 during the pedal's revolution is based on the amount of pressure applied by the user. For example, as the user applies a downward force with his or her foot, the foot pushes on the shoe 12 from within the shoe. This downward force pushes against the first plate 28 and causes the first plate 28 to move with the shoe 12. However, the second plate 30 does not move as much as the first plate 28 in response to the downward force. In other words, there is relative movement between the first plate 28 and the second plate 30. In some examples, the relative movement is caused because second plate 30 is rigidly connected to the pedal 16 through the connection mechanism 18 while the first plate 28 is allowed to move relative to the downward force. In other examples, the sole of the shoe 12 is compressed in response to the downward force causing the first and second plates 28, 30 to move closer.

The pedal 16 can be connected to the gear assembly of a self-propelling bicycle or to a resistance mechanism of a stationary bicycle 10. The movement of the pedal in the self-propelling bicycle may be resisted by an incline of the terrain, friction of the terrain, other terrain conditions, the weight of the bicycle, a load on the bicycle, friction in the gear assembly, other conditions, or combinations thereof. Regardless of the source of the resistance to the movement of the pedal 16, the resistance can cause the second plate 30 to move less than the first plate 28. The more force exerted by the user, the greater the relative movement between the first and second plates 28, 30. Further, the greater the relative movement of the first and second plates 28, 30, the greater the distance between the first and second plate 28, 30.

On the back end of the revolution, the user can pull his or her foot in an upward direction. This type of motion can cause the first and second plates 28, 30 to move apart. For example, as the user pulls up, the shoe 12 pulls up with the user's foot. As the shoe 12 moves in the upward direction due to the forces exerted by the user, the first plate 28 moves upward as well. However, the second plate's movement is be resisted by the pedal 16. As a result, the distance between the first plate 28 and the second plate 30 increases.

The distance between the plates 28, 30 can be recorded based on the capacitance of the circuit. In some examples, the capacitance of the circuit is periodically sampled, and the forces are reconstructed based on the samples. Such samples may be gathered at second intervals, microsecond intervals, intervals spanning multiple seconds, other types of intervals, or combinations thereof. In other examples, a measurement signal of the circuit's capacitance is continuously monitored.

The recorded measurements can be stored temporarily in memory in the shoe 12 and then be transmitted to a remote device 14. Such memory may include a buffer, a cache, another type of short term memory, or combinations thereof. In such examples, the temporarily stored measurements may be sent to the remote device 14 on a periodic basis that allows the measurements to be obtained by the remote device 14 in real time or near real time. For example, a transmitter of the shoe 12 may send the stored data to the remote device 14 at one second intervals, sub-second intervals, microsecond intervals, other types of intervals, or combinations thereof. In other examples, the measurements may be continuously transmitted to the remote device 14.

The data may be processed prior to sending the data to the remote device 14. Such data processing may include compression processing or other types of processing that may reduce the transmission time or the transmission power of sending the data to the remote device 14. In other examples, the signals are not pre-processed prior to sending. The remote device 14 may further process the measurements.

In some examples, the remote device 14 calculates the calories burned, the distance traveled, the speed, and other parameters related to the user's workout based on the pressure measurements. In addition to sending the remote device 14 information from the pressure sensor 22, some examples include sending measurements from the accelerometer 24.

The accelerometer 24 may be positioned in any appropriate location in the shoe 12. The accelerometer 24 may sense motion of the shoe 12 in multiple directions, including upward directions, downward directions, and directions to the side. The accelerometer's measurements may be used to determine if a motion artifact exists in the values collected with the pressure sensor 22. If such a motion artifact exists, the recorded pressures can be modified to reflect the appropriate values without the motion artifact. The accelerometer's measurements may be sent to the memory or directly to the transmitter for conveyance to the remote device 14. In some embodiments, the accelerometer's measurements stay locally within the shoe 12 and are used to modify the recorded pressures prior to sending them to the remote device 14. In other examples, the calculations and other adjustments to be made based on the measurements from the accelerometer 24 are performed at the remote device 14. In other examples, the accelerometer 24 is used to determine the direction of the force applied to the shoe 12.

In some examples, the other information is recorded by other sensors in the shoe 12 or outside of the shoe 12. Such additional measurements may also be sent to the remote device 14. For example, a heart rate monitor 56, an oxygen consumption monitor, a blood pressure monitor, an odometer 58, a speedometer 60, a timer 55, a resistance mechanism 54, another type of sensor, or combinations thereof may send additional information to the remote device 14.

Workout results derived from the information received by the remote device 14 may be presented to the user during his workout in real time or near real time. For example, the calculated information may be displayed in a display of the stationary bicycle 10. In other examples, the information may be displayed in a display that mounts to the handle bars or another component of the self-propelling bicycle. However, in yet other examples, the remote device 14 does not perform calculations on the obtained information, but rather forwards the information to a cloud based network device where the information is accessible to a remote device 14 that can make calculations based on the data. Such a network device may be part of a database that stores information about the user's fitness or exercise activities. In other examples, the remote device 14 forwards the information directly to another device that performs the calculations. In some examples, the results of the calculations are sent back to a local display associated with the bicycle while the user is still performing the workout for providing feedback to the user.

Any appropriate type of communication protocol between the shoe's transmitter and the remote device may be used in accordance with the principles described in the present disclosure. Such protocols may include standard wireless protocols, protocols used by Bluetooth® technologies, Wi-Fi protocols, Z-wave protocols, Zigbee protocols, other types of wireless protocols, or combinations thereof.

In alternative embodiments, the data is stored in the shoe 12 until it is downloaded. In such an example, the stored data may be downloaded after the workout is finished. This allows the user to review his or her results after the workout is concluded. Downloading the data may be accomplished wirelessly. In some examples, a cable can be used to download the data.

Figure 3:
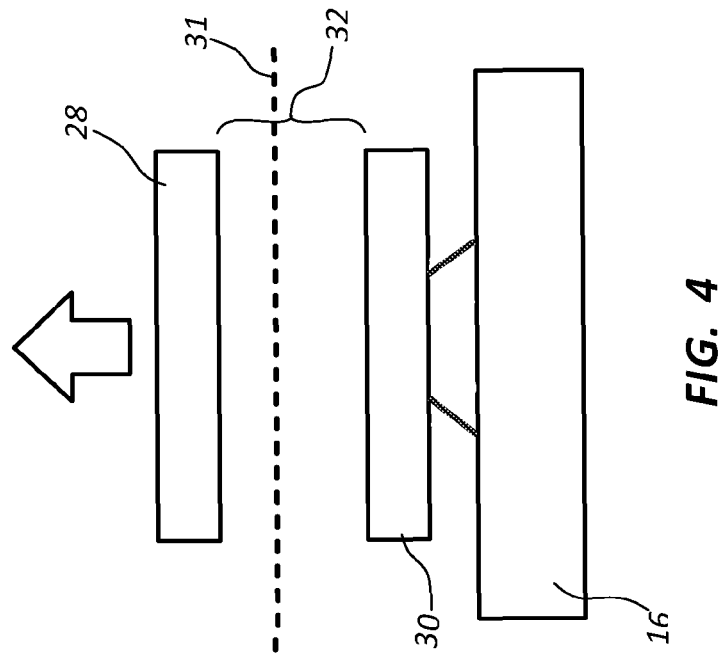
FIG. 3 illustrates a diagram of an example of a pressure sensor in accordance with the present disclosure.
Figure 4:
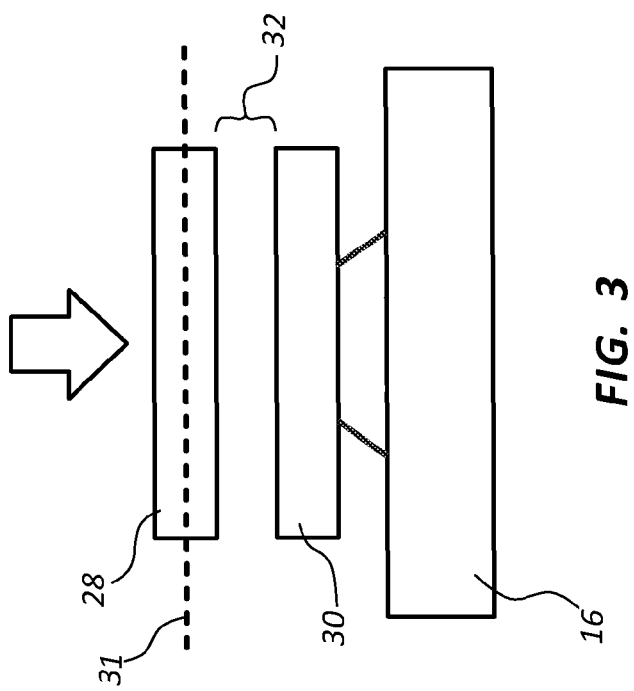
FIG. 4 illustrates a diagram of an example of a pressure sensor in accordance with the present disclosure.

FIGS. 3 and 4 illustrate a pressure sensor 22 in accordance with the present disclosure. In these examples, both the first plate 28 and the second plate 30 of the pressure sensor 22 are disposed within the shoe 12. Additionally, the second plate 30 is rigidly attached to the connection mechanism 18, such as a cleat receptacle. In such examples, when the cleat 27 is interlocked with the cleat receptacle, the second plate 30 is also rigidly attached to the pedal 16. The first plate 28 moves based on the pressures exerted on the sole 26 of the shoe 12. Thus, as the foot exerts an upward force on the shoe 12, the first plate 28 is pulled upwards, which increases the distance 32 between the first plate 28 and the second plate 30. Likewise, as the foot exerts a downward force on the shoe 12, the first plate 28 is pushed downwards, which decreases the distance 32 between the first plate 28 and the second plate 30.

In the illustrated example, the first and the second plates 28, 30 store an electrical charge as part of a circuit. As the distance 32 between the first plate 28 and the second plate 30 changes, the amount of capacitance that the circuit can hold also changes. These capacitive changes can be detected with a capacitance meter, a volt meter, an ammeter, another type of meter, or combinations thereof. As a result, the circuit can exhibit electrical properties that indicate the distance 32 between the plates 28, 30. Thus, as the pressures exerted by the foot cause the plates 28, 30 to move relative to one another, the pressure changes can be sensed by measuring the electrical properties of the circuit.

In some examples, the readings of the pressure sensor 22 indicate whether there is an upward force or a downward force on the pedals. In one approach for determining the direction of the pressure forces, a predetermined baseline distance is selected. A baseline distance between the first plate 28 and the second plate 30 is depicted in FIGS. 3 and 4 with a dashed line 31, which may represents the resulting distance 32 between the plates 28, 30 in the absence of upward or downward forces. In such an example, when there are no forces exerted by the user, the distance 32 between the plates 28, 30 are as though the underside of the first plate 28 rests on the dashed line 31. As a result, when the underside of the first plate 28 is above the dashed line 31, a processing device may determine that there is an upward force on the pedal 16. Likewise, when the underside of the first plate 28 is below the dashed line 31, the processing device may determine that there is a downward force on the pedal 16. In some examples, an electrical property of circuit can correlate with the distance 32 between the plates 28, 30. Thus, a baseline electrical value may be associated with the baseline distance. As a result, a processor may determine whether the force is an upward force or a downward based on whether the electrical property is above or below the baseline value. Further, the processor may understand the amount of force applied in either the upward or downward direction based on how high or how low the measured electrical property is from the baseline value.

In another approach, the processing device may determine that there is an upward force or an downward force by determining whether the distance 32 between the plates is increasing or decreasing. For example, to determine whether a pressure reading associated with a first timestamp is an upward force or a downward force, the processing device may look at a set of distances taken immediately before and/or immediately after the timestamp to determine whether the distances between the plates 28, 30 are increasing or decreasing. If the distance 32 between the plates is increasing, then the processing element may determine that there is an upward force. On the other hand, if the distance 32 between the plates is decreasing, then the processing element may determine that the force is a downward force. As described above, the distance may correspond to an electrical property of the circuit. Thus, in some examples, the direction of the force may be determined by whether the measured electrical property is increasing or decreasing.

In yet another approach, the accelerometer 24 may take measurements to determine whether the pedal 16 is going in an upward direction or a downward direction. In such an approach, measurements from the accelerometer 24 and the pressure sensor 22 may be compared to determine which direction the pedal 16 is moving and assign a direction to the force based on the direction indicated by the accelerometer 24.

In some examples, a pressure sensor 22 and associated components are incorporated into just a single shoe worn by the user. In such a circumstance, the processing device may estimate the forces exerted by the user's other foot. In situations where both shoes worn by the user include the pressure sensor 22 and associated components, the measurements for each shoe 12 can be used to determine the calories and forces specific to the foot exerting the energy. In some examples, a display may indicate which calories, forces, or other parameters are attributable to which foot.

The processing device may have the capability of determining whether the user is pedaling the bicycle, walking, or performing another task. In such an embodiment, the patterns exhibited in the accelerometer's readings and/or the pressure sensor's readings can be analyzed. If it is determined that the user is standing or just walking, the components of the shoe 12 may switch off, discard recorded data, withhold recorded data from the processing device, take another action, or combinations thereof. On the other hand, if the accelerometer's measurements or the pressure sensor's measurements exhibit patterns that suggest that the user is pedaling, the processing device may incorporate the measurements into the calculations for determining a calorie count, stroke specific calculations, torque, other determinations, or combinations thereof. In such examples, the user may start and stop his or her workout without turning on or off the shoe's sensors to avoid integrating non-relevant data into the user's fitness information.

Figure 5:
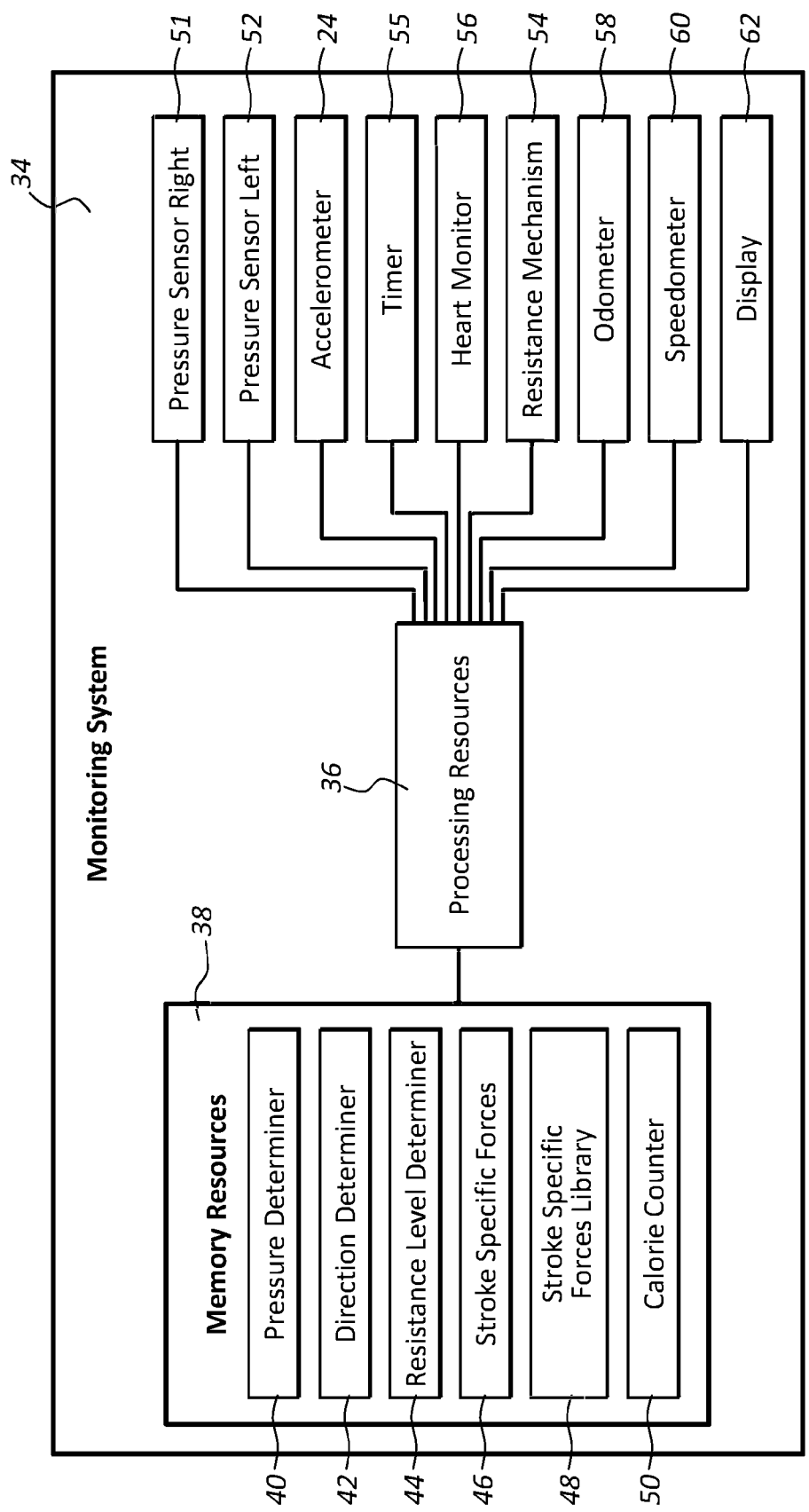
FIG. 5 illustrates a block diagram of an example of a monitoring system in accordance with the present disclosure.

FIG. 5 illustrates a block diagram of an example of a monitoring system 34 in accordance with the present disclosure. The monitoring system 34 may include a combination of hardware and program instructions for executing the functions of the monitoring system 34. In this example, the monitoring system 34 includes processing resources 36 that are in communication with memory resources 38. Processing resources 36 include at least one processor and other resources used to process programmed instructions. The memory resources 38 represent generally any memory capable of storing data such as programmed instructions or data structures used by the monitoring system 34. The programmed instructions shown stored in the memory resources 38 include a pressure determiner 40, a direction determiner 42, a resistance level determiner 44, a stroke specific forces determiner 46, and a calorie counter 50. The data structures shown stored in the memory resources 38 include a stroke specific forces library 48.

The memory resources 38 include a computer readable storage medium that contains computer readable program code to cause tasks to be executed by the processing resources 36. The computer readable storage medium may be a tangible and/or non-transitory storage medium. The computer readable storage medium may be any appropriate storage medium that is not a transmission storage medium. A non-exhaustive list of computer readable storage medium types includes non-volatile memory, volatile memory, random access memory, write only memory, flash memory, electrically erasable program read only memory, magnetic based memory, other types of memory, or combinations thereof.

The pressure determiner 40 represents programmed instructions that, when executed, cause the processing resources 36 to determine the amount of pressure exerted on the pedal 16 based on readings from a right pressure sensor 51 and a left pressure sensor 52. The direction determiner 42 represents programmed instructions that, when executed, cause the processing resources 36 to determine the direction of the pressure exerted on the pedal 16. The direction of the force may be determined based on the readings from the pressure sensors 51, 52. In some examples, the direction of the pressures is determined, at least in part, with an accelerometer 24. The resistance level determiner 44 represents programmed instructions that, when executed, cause the processing resources 36 to determine the amount of resistance applied to reciprocating movement of the pedals based on an output from a resistance mechanism 54. The stroke specific forces determiner 46 represents programmed instructions that, when executed, cause the processing resources 36 to determine forces that are specific to each stroke executed by the user. A non-exhaustive list of stroke specific forces that may be calculated in accordance with the principles described in the present disclosures include torque, revolution speed, calories burned, upward force, downward force, overall force, other types of stroke specific forces, or combinations thereof. These forces may be kept in the stroke specific forces library 48. The calorie counter 50 represents programmed instructions that, when executed, cause the processing resources 36 to track the number of calories burned by the user. The accelerometer 24 may be used to determine when a stroke is completed. A stroke may be an entire revolution, and the accelerometer 24 may record acceleration patterns throughout the revolution. In some examples, as the patterns recorded by the acceleration patterns repeat, the beginning and ending of a stroke can be determined. A timer 55 can associate the measurements with a point in time to assist in determining the time at which the pressure and/or accelerometer measurements were taken.

The calorie counter 50 may use information from the stroke specific library 48, from the pressure sensors 51, 52, the accelerometer 24, a heart rate monitor 56 worn by the user, an odometer 58 mounted to the bicycle, a speedometer 60 mounted to the bicycle, other instruments, or combinations thereof.

The calculated results of the workout can be presented to the user through any appropriate mechanism. In some examples, the calculated results are displayed to the user through a display 62 mounted to the bicycle or a mobile device of the user.

Further, the memory resources 38 may be part of an installation package. In response to installing the installation package, the programmed instructions of the memory resources 38 may be downloaded from the installation package's source, such as a portable medium, a server, a remote network location, another location, or combinations thereof. Portable memory media that are compatible with the principles described herein include DVDs, CDs, flash memory, portable disks, magnetic disks, optical disks, other forms of portable memory, or combinations thereof. In other examples, the program instructions are already installed. Here, the memory resources 38 can include integrated memory such as a hard drive, a solid state hard drive, or the like.

In some examples, the processing resources 36 and the memory resources 38 are located within the shoe 12. The memory resources 38 may be part of the shoe's main memory, caches, registers, non-volatile memory, or elsewhere in the shoe's memory hierarchy. Alternatively, the memory resources 38 may be in communication with the processing resources 36 over a network. Further, the data structures, such as the libraries, may be accessed from a remote location over a network connection while the programmed instructions are located locally. Thus, information from the monitoring system 34 may be accessed from the shoe 12; a user device; a mobile device; a phone; an electronic tablet; a wearable computing device; a head mounted device; a server; a collection of servers; a networked device; a watch; a user interface in a car, truck, plane, boat, bus, another type of automobile; or combinations thereof.

The monitoring system 34 of FIG. 5 may be part of a general purpose computer. However, in alternative examples, the monitoring system 34 is part of an application specific integrated circuit.

Figure 6:
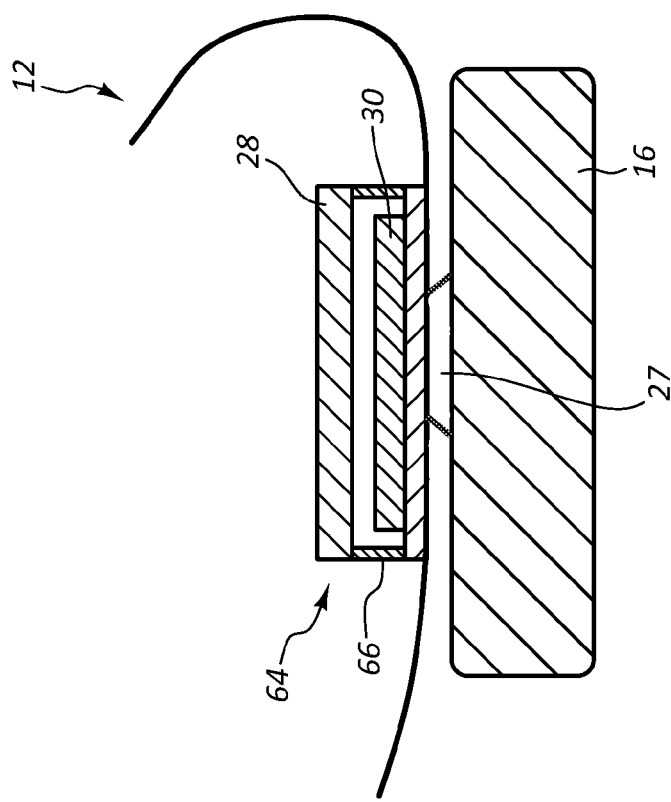
FIG. 6 illustrates a cross sectional view of an example of an energy harvesting mechanism in accordance with the present disclosure.

FIG. 6 illustrates a cross sectional view of an example of an energy harvesting mechanism 64 in accordance with the present disclosure. In this example, the energy harvesting mechanism 64 includes a piezoelectric material 66 that exhibits a characteristic of producing a voltage when mechanically deformed. In such an example, the piezoelectric material 66 receives a portion of the load when the user exerts a downward force through the shoe 12. Under such a load, the voltage is produced, which generates a current. The piezoelectric material 66 is part of a circuit and is oriented to direct the current and/or voltage generated by the deformation of the piezoelectric material 66 towards a power storage unit.

In some examples, the power storage unit is a capacitor that stores the electrical energy until the energy is needed. At such a time, the capacitor discharges enough energy to power the operation. In some examples, multiple components of the monitoring system 34 are operated by the electrical energy discharged by the capacitor. For example, electrical energy may be used to write measurements into a memory stored in the shoe 12, transmit the measurements to the remote device 14, record an accelerometer reading, write values from the accelerometer reading into memory, process the data recorded by the accelerometer 24 and/or pressure sensor 22, perform other functions, or combinations thereof. In other examples, chargeable batteries or other types of power storage units are incorporated into the shoe 12 and are the recipients of the electrical energy from the energy harvesting mechanism 64.

Figure 7:
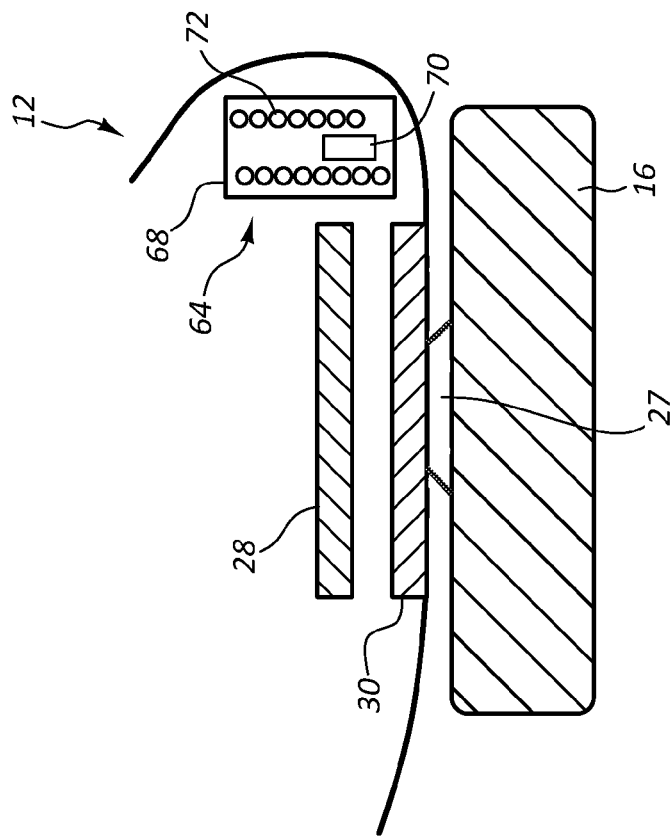
FIG. 7 illustrates a cross sectional view of an example of an energy harvesting mechanism in accordance with the present disclosure.

FIG. 7 illustrates a cross sectional view of an example of an energy harvesting mechanism 64 in accordance with the present disclosure. In this example, the energy harvesting mechanism 64 includes chamber 68 that is shaped to house a reciprocating magnet 70 that travels in response to the movement of the shoe 12. Also, an electrically conductive coil 72 is incorporated into the chamber 68. The electrically conductive coil 72 and the reciprocating magnet 70 are arranged so that as the reciprocating magnet 70 travels in response to the shoe's movement. As the reciprocating magnet 70 travels, it's magnetic field passes through portions of the electrically conductive coil 72, which induces an electrical current. The electrically conductive coil 72 may be incorporated into a circuit that directs the electrical current to the power storage unit, where the stored electrical power can be used for operations of the pressure sensor 22 and other components incorporated into the shoe 12.

Figure 8:
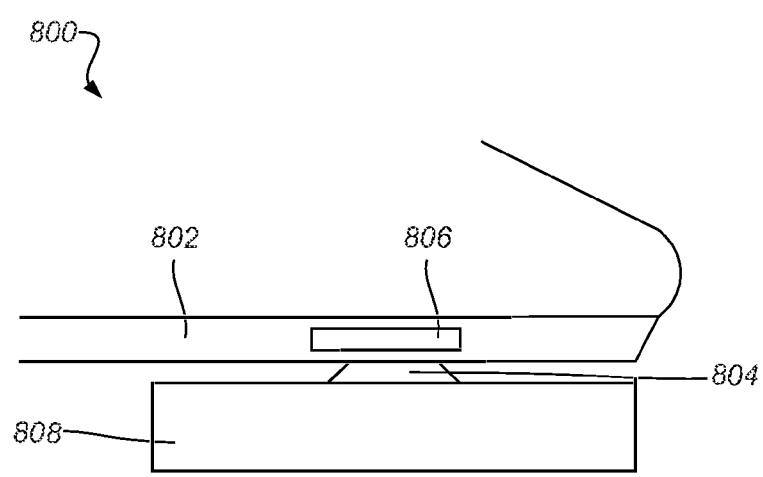
FIG. 8 illustrates a cross sectional view of an example of a monitoring system in accordance with the present disclosure.

FIG. 8 depicts the monitoring system with a shoe 800 and a sole 802 integrated into the shoe 800. A connection mechanism 804 is attached to an underside of the sole 802 and is shaped to connect the sole 802 to a pedal 808. A pressure sensor 806 incorporated into the shoe 800 that senses a force exerted on the pedal 808 when the shoe 800 is connected to the pedal 808 through the connection mechanism 804.

INDUSTRIAL APPLICABILITY

In general, the invention disclosed herein may provide the user with calorie and force calculations associated with the work performed on a bicycle or another foot operated device. The bicycle may be a stationary bicycle or a self-propelled bicycle. The pressure sensor can be incorporated into the shoe proximate the cleat receptacle of a clipless pedal system or another type of system where the shoe is connected to the pedal. The pressure sensor can include at least two plates that move in response to upward forces and/or downward forces exerted by the user while pedaling.

A pressure sensor in accordance with the present disclosure may include a pressure sensor with a first plate and the second plate. In some cases, the second plate is rigidly attached to the connection mechanism, such as a cleat receptacle in the sole of the shoe. In such examples, when the cleat is interlocked with the shoe, the second plate is also rigidly attached to the pedal. The first plate may move based on the pressures exerted on the sole of the shoe. Thus, as the foot exerts an upward force on the shoe, the first plate is pulled upwards, which increases the distance between the first plate and the second plate. Likewise, as the foot exerts a downward force on the shoe, the first plate is pushed downwards, which decreases the distance between the first plate and the second plate.

In the some examples, an electrical circuit is incorporated into the shoe. The electrical shoe includes a first and the second plates that store an electrical charge. As the distance between the first plate and the second plate changes, the amount of capacitance that the circuit can hold also changes. These capacitive changes can be detected with a capacitance meter, a volt meter, an ammeter, another type of meter, or combinations thereof. As a result, the circuit can exhibit electrical properties that indicate the distance between the plates. Thus, as the pressures exerted by the foot cause the plates to move relative to one another, the pressure changes can be sensed by measuring the electrical properties of the circuit.

In some examples, the pressure sensor may indicate whether there is an upward force or a downward force on the pedals. In one approach for determining the direction of the pressure forces, a predetermined baseline distance is selected. A baseline distance between the first plate and the second plate may represents the resulting distance between the plates in the absence of upward or downward forces cause by the turning of the pedal. In such an example, when there are no such forces exerted by the user to turn the pedal, the distance between the plates are at the baseline distance. As a result, when the underside of the first plate is above the baseline distance, a processing device may determine that there is an upward force on the pedal. Likewise, when the underside of the first plate is below the dashed line, the processing device may determine that there is a downward force on the pedal. In some examples, an electrical property of circuit can correlate with the distance between the plates. Thus, a baseline electrical value may be associated with the baseline distance. As a result, a processor may determine whether the force is an upward force or a downward based on whether the electrical property is above or below the baseline value. Further, the processor may understand the amount of force applied in either the upward or downward direction based on how high or how low the measured electrical property is from the baseline value.

In another approach, the processing device may determine that there is an upward force or an downward force by determining whether the distance between the plates is increasing or decreasing. For example, to determine whether a pressure reading associated with a first timestamp is an upward force or a downward force, the processing device may look at a set of distances taken immediately before and/or immediately after the timestamp to determine whether the distances between the plates are increasing or decreasing. If the distance between the plates is increasing, then the processing element may determine that there is an upward force. On the other hand, if the distance between the plates is decreasing, then the processing element may determine that the force is a downward force. In some examples, the distance may correspond to an electrical property of the circuit. Thus, in some examples, the direction of the force may be determined by whether the measured electrical property is increasing or decreasing.

In yet another approach, the accelerometer may take measurements to determine whether the pedal is going in an upward direction or a downward direction. In such an approach, measurements from the accelerometer and the pressure sensor may be compared to determine which direction the pedal is moving and assign a direction to the force based on the direction indicated by the accelerometer.

In some examples, a pressure sensor and associated components are incorporated into just a single shoe worn by the user. In such a circumstance, the processing device may estimate the forces exerted by the user's other foot. In situations where both shoes worn by the user include the pressure sensor and associated components, the measurements for each shoe can be used to determine the calories and forces specific to the foot exerting the energy. In some examples, a display may indicate which calories, forces, or other parameters are attributable to which foot.

The processing device may have the capability of determining whether the user is pedaling the bicycle, walking, or performing another task. In such an embodiment, the patterns exhibited in the accelerometer's readings and/or the pressure sensor's readings can be analyzed. If it is determined that the user is standing or just walking, the components of the shoe may switch off, discard recorded data, withhold recorded data from the processing device, take another action, or combinations thereof. On the other hand, if the accelerometer's measurements or the pressure sensor's measurements exhibit patterns that suggest that the user is pedaling, the processing device may incorporate the measurements into the calculations for determining a calorie count, stroke specific calculations, torque, other determinations, or combinations thereof. In such examples, the user may start and stop his or her workout by turning on or off the shoe's sensors to avoid integrating non-relevant data into the user's fitness information.

The pressure sensor and other components with the shoe can be powered with an energy harvesting mechanism that minimizes or eliminates batteries or an external power source. This reduces the weight of the shoe and spares the user from having to replace the batteries. Such energy harvesting mechanisms can include kinetic capture mechanisms, piezoelectric mechanisms, self-powered generator mechanisms, thermopile mechanisms, or combinations thereof. In some examples, the movement of the shoe causes coils to pass through a magnetic field. Such movement may be achieved through allowing some internal components of the shoe to move relative to other internal components as the shoe moves. For example, a magnet may move relative to coils as the shoe moves. In other examples, the coils may move in relation to a magnetic field. In either example, the differential movement between the coils and the magnetic field may generate an electrical current in the coils, which current may be directed to a battery or directly to the components of the shoe that user electrical power.

The monitoring system may include a shoe and a sole integrated into the sole. A connection mechanism may be attached to an underside of the sole and be shaped to connect the sole to a pedal. A pressure sensor may be incorporated into the shoe that senses a force exerted on the pedal when the shoe is connected to the pedal through the connection mechanism. In some cases, the pressure sensor can distinguish between upward forces imposed on the pedal and downward forces imposed on the pedal.

The measurements of the pressure sensor and the accelerometer (in those embodiments that include an accelerometer) may be transmitted to an external device, such as a mobile device carried by the user while on the exercise machine, another computing device, a network device, another type of device, or combinations thereof. Such a computing device may quantify the forces exerted onto the pedal and use such force determinations to determine a calorie count or another unit of energy consumption performed by the user.

The connection mechanism that connects the shoe to the pedal may be a clipless pedal system where a cleat receptacle of the underside of the shoe interlocks with the cleat from the pedal. The pressure sensor may be disposed proximate the cleat receptacle.

In some cases, the pressure sensor is a capacitive based pressure sensor. In such an example, the capacitive based pressure sensor may comprise electrically conducting plates that are spaced a distance from each other. The electrically conducting plates may move such that the distance between the plates narrows during a downward force on the pedal and the distance widens during an upward force on the pedal.

Any appropriate type of shoe may be used in accordance with the principles described herein. In some examples, the shoe is a cycling shoe that has a sole made of a stiff material to minimize flexing of the sole as a force is transferred from the shoe to the pedal. The clipless pedal system includes a cleat receptacle in the sole of the shoe. The cleat protrudes upward from the pedal and is shaped to interlock with cleat receptacle of the shoe. In some examples, the cleat snaps into a spring loaded mechanism incorporated into the sole of the shoe. The cleat may be made of any appropriate material, such as metal, plastic, or other types of material. Further, the cleat may have any appropriate type of shape to interlock with the shoe's sole.

Any appropriate type of pedal may be used with the shoe as long as the pedal is capable of interlocking with the shoe through the connection mechanism. In some examples, the pedal can interlock with the shoe on both faces of the pedal, while in other examples, the pedal can interlock with just a single face of the shoe.

What is claimed is:

1. A method for monitoring pedaling, comprising:
   placing a first plate above a second plate in a sole of a shoe;
   determining a baseline distance between the first plate and the second plate in the absence of an upward force or a downward force on the sole;
   determining the upward force based on a user moving the first plate away from the second plate during a pedal stroke resulting in a first distance between the first plate and the second plate, the first distance being greater than the baseline distance; and
   determining the downward force based on the user moving the first plate toward the second plate during the pedal stroke resulting in a second distance between the first plate and the second plate, the second distance being less than the baseline distance.

2. The method of claim 1, further comprising associating a capacitance with the baseline distance.

3. The method of claim 2, wherein determining the baseline distance includes determining a baseline capacitance for the baseline distance.

4. The method of claim 3, wherein determining the upward force includes determining whether a measured capacitance is less than the baseline capacitance.

5. The method of claim 4, further comprising determining an amount of the upward force based on how much the measured capacitance is below the baseline capacitance.

6. The method of claim 3, wherein determining the downward force includes determining whether a measured capacitance is greater than the baseline capacitance.

7. The method of claim 6, further comprising determining an amount of the downward force based on how much the measured capacitance is above the baseline capacitance.

8. A method for monitoring a user, comprising:
   measuring a first distance between a first plate placed above a second plate in a sole of a shoe at a first timestamp;
   measuring a second distance between the first plate and the second plate at a second timestamp, the second distance being different than the first distance based on a user moving the first plate relative to the second plate during a pedal stroke; and
   determining a direction of a force applied to the sole based on a difference between the first distance and the second distance.

9. The method of claim 8, wherein determining the direction of the force includes determining that the force is an upward force when the user moves the first plate away from the second plate such that the first distance is greater than the second distance and that the force is a downward force when user moves the first plate toward the second plate such that the first distance is less than the second distance.

10. The method of claim 8, wherein measuring the first distance includes measuring a first capacitance and wherein measuring the second distance includes measuring a second capacitance.

11. The method of claim 10, wherein determining the direction of the force includes determining that the force is an upward force when the first capacitance is greater than the second capacitance and that the force is a downward force when the first capacitance is less than the second capacitance.

12. The method of claim 8, further comprising determining an exercise performed by said user by analyzing a pattern of measured distances.

13. The method of claim 8, further comprising determining an amount of calories burned by said user based on a pattern of measured distances.

14. The method of claim 8, further comprising wirelessly transmitting the first distance and the second distance to a remote computing device.

15. The method of claim 14, wherein wirelessly transmitting the first distance and the second distance includes at least partially processing the first distance and the second distance in the shoe before wirelessly transmitting.

16. A monitoring system, comprising:
   a shoe including a sole;
   a connection mechanism attached to an underside of the sole, wherein the connection mechanism is shaped to connect the sole to a pedal; and
   a pressure sensor including a first plate and a second plate spaced apart from the first plate to form a capacitor, wherein the pressure sensor is incorporated within the sole of the shoe that senses a force exerted on the pedal when the shoe is connected to the pedal through the connection mechanism, wherein the first plate is located above the second plate, a baseline distance between the first plate and the second plate representing a distance between the first plate and the second plate in the absence of an upward force and a downward force, and the pressure sensor determines that a user has applied an applied upward force during a pedal stroke based on if the user moves the first plate away from the second plate such that the distance between the first plate and the second plate is greater than the baseline distance and the pressure sensor determines that the user has applied an applied downward force during the pedal stroke if the user moves the first plate toward the second plate such that the distance between the first plate and the second plate is less than the baseline distance.

17. The monitoring system of claim 16, wherein the shoe includes an accelerometer.

18. The monitoring system of claim 17, wherein the accelerometer measures a motion of the shoe in at least three directions.

19. The monitoring system of claim 16, further comprising computing device including a processor and memory, the memory including programmed instructions that cause the processor to quantify the force based at least in part on the measurements of the pressure sensor.

20. The monitoring system of claim 19, wherein the programmed instructions further cause the processor to quantify a calorie count based at least in part on the measurements of the pressure sensor.

* * * * *